United States Patent [19]
Duncan et al.

[11] Patent Number: 5,750,009
[45] Date of Patent: May 12, 1998

[54] METHOD FOR PURIFYING NATURAL CRESYLIC ACID MIXTURES

[75] Inventors: David H. Duncan, Beulah; Gene G. Baker, Hazen; Alfred K. Kuhn, Beulah; Dana J. Maas; Kevin M. Mohl, both of Hazen, all of N. Dak.

[73] Assignee: Dakota Gasification Company, Beulah, N. Dak.

[21] Appl. No.: 653,815

[22] Filed: May 28, 1996

Related U.S. Application Data

[63] Continuation of Ser. No. 298,835, Aug. 31, 1994, abandoned.

[51] Int. Cl.⁶ ............................. B01D 3/40; C07C 37/74
[52] U.S. Cl. ............................. 203/64; 203/14; 203/78; 568/750
[58] Field of Search ............................. 203/14, 64, 78, 203/DIG. 9, 75.18; 568/750, 756, 759, 761

[56] References Cited

U.S. PATENT DOCUMENTS

| | | | |
|---|---|---|---|
| 2,666,796 | 1/1954 | Gorin et al. | 260/627 |
| 2,767,220 | 10/1956 | Neuworth | 260/627 |
| 2,789,145 | 4/1957 | Neuworth | 260/627 |
| 3,075,890 | 1/1963 | Chambers et al. | 202/39.5 |
| 3,079,326 | 2/1963 | Neuworth | 208/45 |
| 3,331,755 | 7/1967 | Neuworth | 203/59 |
| 4,349,418 | 9/1982 | Belsky et al. | 203/46 |
| 4,429,170 | 1/1984 | Lovell | 568/761 |
| 4,443,636 | 4/1984 | Greco | 568/761 |
| 5,171,895 | 12/1992 | Brient | 568/749 |
| 5,354,429 | 10/1994 | Duncan et al. | 203/64 |

FOREIGN PATENT DOCUMENTS

| | | | |
|---|---|---|---|
| 204 474 | 11/1983 | Germany | 37/74 |
| 49731 | 8/1993 | Japan | |
| 895119 | 5/1962 | United Kingdom | 2/3 |

OTHER PUBLICATIONS

English Translation of German Patent Document 204 474.

*Primary Examiner*—Virginia Manoharan
*Attorney, Agent, or Firm*—Alix, Yale & Ristas, LLP

[57] ABSTRACT

A process for the purification of natural cresylic acid feedstocks which are first depitched. The depitched feedstock is extractively distilled with a polyhydric alcohol, preferably triethylene glycol, to remove virtually all neutral oil species which are indigenous to the phenol and cresol boiling ranges, most of the neutral oil species in the 2,4–2,5-xylenol boiling range, and a significant portion of the neutral oil species of the high boiling xylenol fraction (including of 2,3-xylenol, 3,5-xylenol, para-ethylphenol, meta-ethylphenol, 3,4-xylenol, and numerous $C_9$ phenols). This process is also capable of removing tar bases such as pyridine and its alkyl homologues. This invention is capable of providing a cresylic acid mixture from which it is possible to fractionate phenol, as an overhead product, having only 30 to 60 ppm of neutral oil and negligible tar base content, and providing dephenolized cresylic acid, as a bottoms product, having less than 10% of the neutral oil and less than 20% of the tar bases as would be provided by the same feedstock, if left untreated.

5 Claims, 1 Drawing Sheet

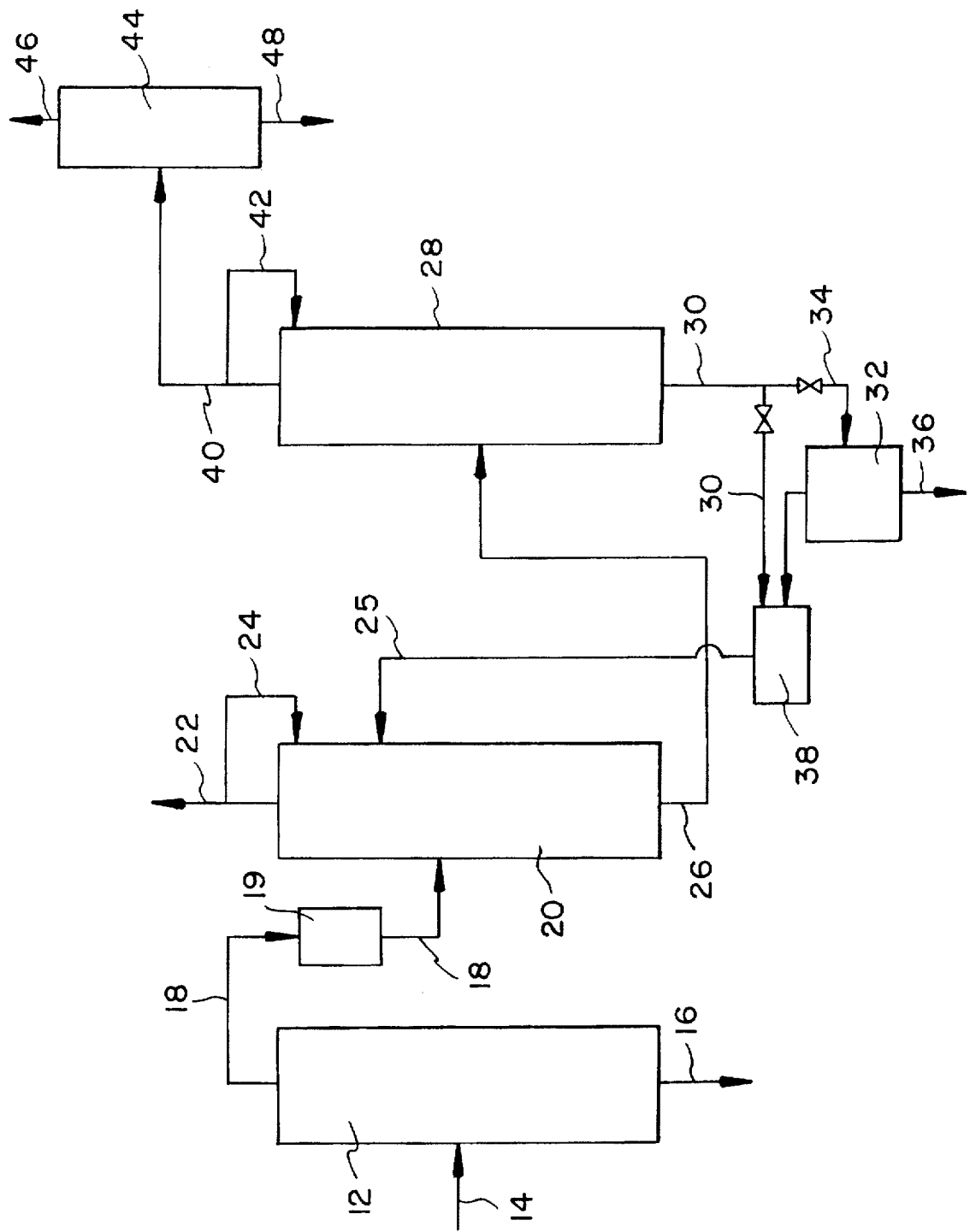

METHOD FOR PURIFYING NATURAL CRESYLIC ACID MIXTURES

This is a continuation of application Ser. No. 08/298,835, filed on Aug. 31, 1994, abandoned.

FIELD OF THE INVENTION

The present invention relates to a method for the removal of neutral oil and tar base impurities from a natural cresylic acid feedstock to produce a purified natural cresylic acid mixture.

BACKGROUND OF THE INVENTION

The natural cresylic acids are derived from either coal or petroleum processing. In petroleum processing, a spent caustic is derived via caustic extraction of phenols from oil refinery distillate products and it is this spent caustic that is processed into a cresylic acid feedstock. Coal-derived feedstocks come from coal process technologies such as coking, gasification or other coal devolatilization processes.

The gas liquor streams which result from cooling of raw gas, and condensation of moisture contained in the raw gas from a coal gasifier, are usually rich in dissolved phenolics. Such aqueous condensate streams are typically subjected to a solvent extraction process in order to extract the phenols from the water. The extraction solvent is then distilled from the phenols and recycled. Typical of these process technologies is the Phenosolvan process, which utilizes diisopropyl ether or a similar solvent as the extraction solvent. Along with the raw gas liquor stream, an organic phase is also condensed, which becomes tar oil after it is decanted.

A typical Phenosolvan extract mixture of phenols, known as crude phenol, usually contains approximately 60 to 75% monohydric phenols (cresylic acid), and may also contain dihydric phenols (such as catechol), along with pitch (20% to 30%), neutral oil (1% to 4%), tar bases (1% to 3%) and water (2% to 6%). Processing to upgrade phenolic extracts derived from such gasification process water (gas liquor) should first include a process step for separation of the monohydric phenols from the dihydric phenols and pitch. This separation is typically accomplished by way of a depitching distillation step. The initial processing may also include a drying step for separation of water and light neutral oils via distillation although that is not necessary for the present invention.

The monohydric phenols cut, thus isolated, contains about 1.5 to 4% tar bases and 1.5 to 5% neutral oil. This phenolic mixture is too impure for most applications, and requires processing for purification. It is, however, a moderately pure material compared to coal tar middle oil distillate, which is much more rich in neutral oil than cresylic acid.

Coal tar middle oil distillate can be obtained from the above-mentioned tar oil stream via distillation. This fraction contains cresylic acid in the 30 to 40% range, the remainder being predominantly neutral oil as well as some tar bases. Natural cresylic acid can be derived from processing such a coal tar middle distillate oil. Given this high a level of impurities, though, some form of pre-concentration of the phenolics is required before the present invention is considered economical to produce a cresylic acid stream low in neutral oil and tar bases.

Natural cresylic acid feedstocks contain phenol, cresols, ethylphenols, xylenols and $C_9$ phenolics. Such raw cresylic acid feedstocks also contain neutral oil and tar base impurities. Neutral oil is a class of organic impurities, each one of which is neither an acid nor a base, such as indenes, indans, ketones and naphthalenes. The tar bases constitute a class of organic impurities, each member of which is a nitrogen-containing compound which behaves as a base, such as pyridine, alkylpyridines, aniline and alkylanilines.

The early methods of purifying natural cresylic acid consisted of reacting the phenols with caustic soda, followed by steam stripping to remove neutral oil and tar bases, and then springing the cresylic acid with carbon dioxide. This is the only prior technology capable of removing both classes of impurities simultaneously in a single process step. This process, including the calcium hydroxide systems employed for regeneration of sodium hydroxide from aqueous sodium carbonate, is quite bulky and energy intensive. An alternative to regeneration of the caustic soda is to dispose of the large quantities of aqueous sodium salt which are produced as a by-product of the step wherein the steamed caustic cresylate is acidified. This material can also be sold as a by-product. In an effort to become more economical and energy efficient, subsequent technologies for purification of wide boiling range cresylic acid mixtures have relied upon separate processes to remove each of the two classes of impurities.

Numerous technologies for the separation of neutral oils from cresylic acid, either alone, or perhaps with a modest amount of tar bases, have relied upon any of a variety of forms of liquid/liquid extraction. Both single solvent and dual solvent pairs have been proposed and used. None of the solvent systems for neutral oil removal are simultaneously capable of greatly diminishing the tar base content. The methods for tar base removal are all a separate step from the neutral oil extraction step and have all relied upon acids in one form or another.

The single solvent methods to extract phenols from a neutral oil matrix have employed aqueous solutions of a number of solvents, such as glycols, ethanolamine, ammonia, acetic acid, ethylamine, sodium salicylate or methanol. Hot water was another single-solvent approach that was used. The solvents were usually removed from the extract mixture by way of distillation and recycled to the front end of the process. All of these technologies were limited in ability to obtain adequate cresylic acid product purity, as well as acceptable cresylic acid recovery. The phenols which were isolated via these technologies contained significant amounts of residual neutral oil contaminants and tar bases. This problem was especially prevalent when a high yield was obtained. With high product yields it was inevitable that large amounts of neutral oil and tar base impurities would be found in the solvent phase.

Because of the purity vs. yield problems of the single-solvent techniques, dual-solvent, fractional liquid-liquid extraction techniques were developed. These technologies provided the ability to obtain low neutral oil content and high yield at once, by using a pair of solvents, one being a polar solvent and the other being a non-polar solvent.

Distillation techniques were used to recover both polar and non-polar solvents for recycle. Like the single solvent techniques, none of these technologies could achieve a good separation of tar bases from cresylic acid. The cresylic acid materials derived from dual solvent processing required a second treatment step to remove tar bases prior to sale as a mixed cresylic acid finished product, or prior to fractionation to obtain finished individual distillate products.

Other types of dual solvent-like processes which were developed were the Phenoraffin process and others similar to it. In this technology, saturated aqueous sodium cresylate served as the polar solvent, and toluene or the like was used in a second extraction step as the non-polar solvent. The sodium cresylate solution, which became oversaturated with dissolved free phenols, was boiled in order to steam distill toluene, and some of the neutral oil not removed in the primary extraction step. A solvent, such as diisopropyl ether, was then used to extract the free phenols from the sodium cresylate solution, thus regenerating it for recycle to the front end of the process. The isopropyl ether solution containing dissolved phenols was then extracted with aqueous sulfuric acid to remove tar bases, and finally the ether was distilled for recycle, leaving the purified cresylic acid as bottoms product.

The East Germans developed technologies based upon the use of calcium hydroxide for purification of cresol mixtures. Cresols were mixed with water, heated, and then reacted with calcium hydroxide to form the water soluble calcium cresolate salt. This aqueous salt was filtered and then further diluted with water to cause neutral oils to be liberated from the solution as a black oily liquid. The product cresolate solution was then acidified with hydrochloric acid in order to free the cresols, making them ready for drying and depitching.

Since only the earliest of the foregoing technologies was capable of removing tar bases, a number of tar base removal processes were developed. Various methods for removal of tar bases, essentially alone, or perhaps including a modest amount of neutral oil, have relied upon the use of mineral acids in one form or another. The most elementary was a process which could be called the acid flash distillation process.

Sulfuric (or more rarely phosphoric) acid was added to cresylic acid and this mixture was distilled in either a batch still or a continuous flash drum. The tar bases were rendered non-volatile via salt formation with the sulfuric acid, and were collected as a bottoms product. The overhead product was obtained as a very nearly tar-base-free material. Alternately, an acidic salt can be used in this kind of process.

A unique version of the acid flash process removed tar bases from phenols by adding sulfuric acid to the fractionation tower while it was being used to fractionate the distillate products which can be manufactured from cresylic acid. Another variation of the acid flash process was very similar to the continuous version of the traditional acid flash method, except that water was used in the distillation to limit the temperature of the process and thus limit the degradation of phenols to tar-like residue.

Another process for the removal of tar bases described a process wherein a cresylic acid distillate fraction was mixed with a strong acid and some toluene or other aromatic substance and cooked for a time. This was followed by a distillation wherein the overhead product, cresylic acid, was treated with activated alumina. The tar base/toluene condensation products were removed as a bottoms product.

In a dissociative extraction process, cresylic acid was dissolved in a solvent, such as chlorobenzene or 2-ethylhexanol, and this mixture was extracted in a countercurrent fashion with aqueous hydrochloric acid. The solvent was distilled from the phenols and recycled. Tar bases were removed from the extraction column as the hydrochloride salts. Some processes also use a strongly acidic cation exchange resin or acidic clays to remove tar bases from cresylic acid. In other processes, tar bases are extracted into an aqueous acid from a solution containing cresylic acid dissolved in a solvent.

The greatest disadvantage encountered with the use of acidic treatments to remove tar bases is the production of acidic tar or acidic aqueous waste streams which are difficult to remediate or dispose of. It is very challenging (or impossible) to recover the tar bases as a valuable by-product from these types of process technologies. Another problem often encountered with these methods is loss of product (cresylic acid) due to undesirable side reactions (e.g., which occur during distillation of cresylic acid with acids), or loss of cresylic acid to solubility in a dilute acidic aqueous stream (either an extract or regenerant stream).

The cresylic acid industry in the past focused almost exclusively upon purification technologies which treat a broad boiling-range mixture of phenols ($C_6$ through $C_9$), derived from either coal or petroleum, in order to separate impurities from such mixtures. Once free of neutral oil and tar base impurities, cresylic acid mixtures were either sold as such, or fractionated into individual distillate products and then sold. At times, such distillate products were processed for even further upgrading.

Such further upgrading of the individual distillate fractions from natural cresylic acid mixtures almost exclusively dealt with the topic of further separations of phenolic substances from one another which cannot be accomplished via ordinary fractionation. Feedstocks for such phenolic separation technologies have been distillate fractions derived via fractionation of essentially tar-base- and neutral-oil-free phenolic mixtures.

U.S. Pat. No. 3,331,755 describes glycol extractive distillation for removal of 2,6-xylenol, an unwanted phenolic substance from m/p-cresol, which is a discrete distillate fraction derived from cresylic acid. At the plant site of the company to which this patent is assigned, it is known that the acid flash process was used for removal of tar bases from a wide boiling range mixture of phenols prior to fractionation to isolate the m/p-cresol distillate fraction. Earlier, this same company had developed the dual solvent technology described in U.S. Pat. Nos. 2,666,796 and 3,079,326 for removal of neutral oil from a coal derived middle oil distillate, which is a wide boiling range mixture. A similar dual solvent technology was used at this plant site to process oil refinery spent caustic-derived cresylic acid. This technology is disclosed in U.S. Pat. Nos. 2,767,220 and 2,789,145.

Extractive distillation of a cresylic acid fraction with glycols was also described in East German Patent No. DD 204,474, for removal of guaiacol from the m/p-cresol fraction via glycol extractive distillation. This patent also described the partial removal of ortho-ethylphenol from m/p-cresol. This cresylic acid processor used the above-described process for tar base removal wherein sulfuric acid was added to the fractionation tower which was producing distillates such as m/p cresol. This same processor also patented the above-described calcium cresolate method for separation of cresols from neutral oil (British Patent 895,119, dated May 2, 1962).

U.S. patent application Ser. No. 086,753 filed Jul. 2, 1993, now U.S. Pat. No. 5,354,429 discloses a method of processing a natural cresylic acid feedstock containing tar base and/or neutral oil substances by first fractionally distilling the feedstock to yield a plurality of discrete fractions each containing the tar base and/or neutral oil substances. Each fraction is then extractively distilled with a polyhydric alcohol solvent. The solvent extracts the discrete fraction from the tar base and neutral oil substances and the discrete fraction is then separated from the solvent by distillation. This patent application contains an expanded description of the origins of natural cresylic acid and much of the history of prior technologies for the removal of neutral oil and tar bases.

SUMMARY OF THE INVENTION

The method of the present invention utilizes an extractive distillation process for the removal of neutral oil and tar bases from a wide boiling range natural cresylic acid mixture ($C_6$ to $C_9$). Such natural cresylic acid mixtures include coal tar-derived fractions which preferably have less than 30% neutral oil and less than 10% tar bases. Spent caustic-derived mixtures, fairly low in neutral oil and tar bases, are also appropriate feedstocks. A high boiling polar solvent is employed to extractively distill both the tar bases and neutral oil, as an overhead product, from the wide boiling range cresylic acid mixture. A depitching distillation step prior to extractive distillation removes the materials boiling higher than the $C_9$ phenols. After the extractive distillation, the purified cresylic acid mixture is separated from the polar solvent by distillation. A slipstream is taken from the solvent bottoms product, and this is depitched to remove tarry materials which build up. The depitched solvent is blended with the remainder of the bottoms stream, and recycled. The phenol may be removed from the natural cresylic acid prior to extractive distillation, or separated from the $C_7$ to $C_9$ cresylic acid components by distillation after such treatment.

BRIEF DESCRIPTION OF THE DRAWING

FIG. 1 is a block flow diagram of the preferred embodiment of the process of the present invention.

DESCRIPTION OF THE PREFERRED EMBODIMENTS

The wide boiling range of natural cresylic acid presents a challenge to the ability of extractive distillation to achieve any sort of useful results in removing neutral oil and tar base impurities. The wide boiling range is exemplified by the fact that the lowest boiling substance (phenol) has a boiling point 43° C. lower than the highest boiling substances (such as 3.4-xylenol). Since at least some of the impurities boil at about the same temperatures as the highest boiling cresylic acid fraction (the xylenols and $C_9$'s), the process must be capable of altering the relative boiling points of the highest boiling of the impurities, relative to phenol, to effect a satisfactory degree of purification.

The process of the present invention preferably begins with a pretreatment distillation step, shown at 12 in the drawing, where the raw cresylic acid feed 14 is depitched by fractional distillation to remove those substances with boiling points in excess of the $C_9$ phenolics. These materials are removed as a bottoms pitch 16.

The overhead 18 from the distillation column 12 containing the natural cresylic acid with the neutral oil and tar base impurities is fed to the extractive distillation column 20 at a suitable column location. Additional processing steps 19 may be included, as will be explained hereinafter. A polyol extractant, preferably triethylene glycol which has a sufficiently high boiling point, is introduced at 25 to the column 20 at a point above the feed line 18. This column is preferably operated at an overhead pressure of about 26.7 kPa (200 mm Hg). Lower pressure could be used (perhaps down to about 1 kPa) but that would normally mean an increased column diameter, and with higher pressures, (perhaps as high as about 80 kPa) glycol and product degradation would tend to be a problem.

The triethylene glycol at the specified column pressures remains, for the most part, in the liquid phase and descends the column where it tends to hydrogen bond with the phenolics, thus reducing their volatility. The volatilities of the neutral oil substances and the tar bases are much less affected by the presence of the glycol, permitting the majority of them to be removed from the column as an overhead distillate product 22 with a portion being refluxed at 24. The bottoms product 26 is a mixture of the phenolics and the glycol or other polyol. The phenolic portion of the bottoms product is greatly reduced in neutral oil and tar base content. The feed to the extractive distillation column 20 may be dried prior to the extractive distillation, or it may contain significant amounts of water without materially affecting the performance of the process.

The bottoms from the extractive distillation column 20 is fed to a fractional distillation column 28 which is used to remove the purified wide boiling range cresylic acid mixture from the glycol or other polyol. The glycol is obtained as bottoms product 30 from this column 28. It is preferable to operate this column at vacuum conditions of about 5.3 kPa (40 mm Hg). Again, lower pressures (down to about 0.5 kPa) could be used with appropriate equipment changes and higher pressure (up to about 40 kPa) operation could be achieved with the attendant glycol and product degradation problems.

A portion of the bottoms 30 from the distillation column 28 is fed to a small column or falling film evaporator 32. This device is used as a reclaimer to distill a glycol slipstream 34 taken from the recycling glycol 30 in order to separate the glycol from pitch-like substances which are formed in the process and which are withdrawn at 36. It is preferable to operate this column at vacuum conditions. The recovered glycol is fed to the extractant feed tank 38 along with the remainder of stream 30.

The purified cresylic acid product from column 28 is withdrawn overhead at 40 with a portion 42 being refluxed. The purified cresylic acid product is sufficiently pure for many applications. It may be further subjected to any of a number of known tar base removal technologies, any of which could be used to complete the removal of aniline and its homologues, which constitute only about 10% or less of the original tar bases present in the feedstock. Additionally, this mixture may also be fractionated at 44 in a manner typical for the cresylic acid industry, to provide phenol stream 46, virtually nil in pyrrole-type tar bases, and having only 30 to 60 ppm of neutral oil substances, and to provide a dephenolized cresylic acid stream 48 having only about 0.16% neutral oil and about 0.25% tar bases.

The following example illustrates the use of triethylene glycol in extractive distillation of depitched natural cresylic acid feedstocks, for neutral oil and tar base removal. The example reflects the preferred 70mole percent triethylene glycol concentration on the phenolic feed stage, but the concentration optionally varies from 10 mole percent to 90 mole percent, and is preferably in the 50 to 80 percent range.

EXAMPLE

A wet cresylic acid feedstock was prepared by distilling crude Phenosolvan extract to separate the monohydric phenols from the pitch and dihydric phenols. This operation is accomplished by conventional fractionation, and is governed by the requirements that the monohydric phenols are at minimal concentration in the pitch bottoms product, and that the dihydric phenols are sharply limited in the overhead product, which is the depitched wet cresylic acid distillate feedstock. This raw cresylic acid feedstock has the analysis reflected in Table 1.

TABLE 1

| RAW CRESYLIC ACID COMPOSITION | |
|---|---|
| total neutral oil species | 1.90% |
| naphthalene | 0.17% |
| acetophenone | 0.05% |
| 1-methylnaphthalene | 0.09% |
| 2-methylnaphthalene | 0.04% |
| other neutral species | 1.55% |
| total tar base species | 1.70% |
| water content | 3.80% |
| phenol | 49.5% |
| total cresols | 31.0% |
| total xylenols | 5.1% |
| total ethylphenols | 3.4% |
| other phenolic species | 2.8% |
| total $C_9$ phenols | 0.8% |
| total phenolics | 92.6% |

For the above analysis, several neutral oil species were selected to quantitate separately in order to monitor the process performance as it pertains to the purity of the various possible end product distillate fractions. The naphthalene is a neutral specie which distills, during fractionation of cresylic acid, along with the cresols; the other selected individual species boil along with the high boiling xylenols/ethylphenols fraction.

In total, 0.98 cubic meters (5 drums) of this material totaling 1020.6 kg. (2,250 lbs.) were charged to the feed tank of a 15 cm diameter pilot plant continuous extractive distillation column. The feed was pumped to the 16th stage of a 23 stage tower configuration at the rate of 22.7 kg. (50 lbs.) per hour. Triethylene glycol was fed to the 19th stage at the rate of 90.7 kg. (200 lbs.) per hour in order to maintain 70 mole % triethylene glycol on the cresylic acid feed stage. The pressure profile across the structured packing was such that the overhead pressure was 26.6 kPa (200 mm Hg) absolute, and the reboiler pressure was 28 kPa (210 mm Hg), given a boilup rate corresponding to 3515 to 4100 watts (12,000 to 14,000 Btu/hr.) heat input. After equilibration of the column, during which time products were recycled to feed and solvent tanks, collection of overhead product began at a reflux ratio of 1:1. After product collection began, about 2.0 kg. (4.5 lbs.) per hour of overhead product was withdrawn, and 111.1 kg. (245 lbs.) per hour of bottoms product was withdrawn.

The bottoms product was directly pumped to the 6th stage of a recovery distillation tower 28 configured to have a total of 12 stages. The feed rate was 111.1 kg. (245 lbs) per hour, and the overhead pressure was 5.3 kPa (40 mm Hg), and the reboiler pressure was 9.3 kPa (70 mm Hg) absolute, given a boilup rate corresponding to a heat input in the range of 8200 to 8790 watts (28,000 to 30,000 Btu/hr.). After equilibration of this column, which occurred during the same time as for the first column, a reflux ratio of 1.4:1 was employed to begin collection of the overhead product, which was the purified cresylic acid. While the system was in equilibrium, 20.4 kg. (45 lbs.) per hour of overhead product was collected, and 90.7 kg. (200 lbs.) per hour of bottoms product was collected.

A glycol slipstream 34 of 9.1 kg. (20 lbs) per hour, taken from the bottoms product line 30 from the recovery tower, was fed to a glycol recovery distillation column 32 in order to depitch the glycol. This glycol depitcher may be as simple as a 1 theoretical stage flash still, or may contain additional stages. The bottoms product from this glycol depitcher was drawn off at a rate of 0.09 kg. (0.2 lbs.) per hour. The choice of drawdown rate from the depitcher reboiler was determined by the glycol concentration in the pitch. The rate of drawdown was such that the glycol concentration in the pitch was maintained at about 50%, which limited the viscosity of the pitch to a reasonable value, permitting it to be pumped. The overhead product from this regeneration column, depitched glycol, was not refluxed. It was withdrawn at 8.9 kg. (19.8 lbs.) per hour, and pumped to the solvent feed tank 38.

The overhead product from the recovery tower, the purified cresylic acid, was collected in drums. This material had a composition as shown in Table 2.

TABLE 2

| PURIFIED CRESYLIC ACID COMPOSITION | |
|---|---|
| total neutral oil species | 0.0820% |
| naphthalene | 0.0018% |
| acetophenone | 0.0021% |
| 1-methylnaphthalene | 0.0240% |
| 2-methylnaphthalene | 0.0189% |
| other neutral species | 0.0352% |
| total tar base species | 0.130% |
| phenol | 53.3% |
| total cresols | 33.5% |
| total xylenols | 5.5% |
| total ethylphenols | 3.7% |
| other phenolic species | 3.0% |
| $C_9$ phenols | 0.8% |
| total phenolics | 99.8% |

These results show that about 96% of the total neutral oil was removed, given the stated extractive distillation conditions. The only tar bases remaining in this cresylic acid were the aniline homologues, and these, as shown in Table 2, were found at a concentration of only 0.13%. From this it can be seen that over 92% of the tar bases were removed from the cresylic acid at the stated extractive distillation conditions. A small amount of cresylic acid was found in the impurities stream, which is the product 22 of the extractive distillation step.

Typically, the recovery of cresylic acid in this process is in the range of 98% to 99%. Although the feedstock used in this example was a depitched Phenosolvan extract stream, which is a coal gasification by-product, other phenolic-rich natural cresylic acid feedstocks which have been properly depitched benefit in the same manner from the invention.

The feedstock for the present invention may by dried prior to the extractive distillation such as by distilling off the water. However, by allowing the extractive distillation step to assume the burden of water removal, the need to build a separate water removal column is eliminated. It may also be desirable in certain situations to distill off the phenol and perhaps even the cresols before the extractive distillation. Additionally, the process would accommodate a feedstock from which the tar bases had been removed, in which case the benefit obtained by the process would be the neutral oil removal. Such pretreatments are diagrammatically illustrated at 19 in the drawing.

In addition to the recovery of the cresylic acid, the polyol extractive distillation as a means for removal of tar bases also results in the production of a by-product stream which is not contaminated with high-boiling tar-like material or mineral acids and is sufficiently concentrated in tar base content to be easily amenable to recovery of the valuable tar bases as saleable products.

The present process of a polyol extractive distillation process for removal of neutral oil and tar bases from a wide boiling range natural cresylic acid mixture is a significant advance in the art of cresylic acid processing, given that it is capable of greatly diminishing the neutral oil and tar base content of natural cresylic acid in a single process technology, rather than in multiple processes, and given that it accomplishes this without resorting to the use of sodium salt formation. This process is less energy intensive than the prior art, does not result in the formation of large volumes of waste streams, and provides an impurities stream amenable to recovery of the tar bases as saleable by-products.

We claim:

1. A process for producing a purified natural cresylic acid mixture including in its boiling range a mixture of phenols including at least the $C_7$ through $C_9$ phenols comprising the steps of:

a. distilling a natural cresylic acid feedstock containing said mixture of phenols and pitch materials boiling higher than said $C_9$ phenols and at least one member selected from the group consisting of tar base substances and neutral oil substances to separate said pitch materials from said feedstock and producing a depitched feedstock containing said mixture of phenols and said member;

b. extractively distilling said depitched feedstock consisting essentially of the entire said mixture of phenols and said member with a polyhydric alcohol solvent, said solvent having a boiling point sufficiently higher than said depitched feedstock with which it is used to permit subsequent separation therefrom, whereby said member is separated from said solvent containing said mixture of phenols;

c. subsequently separating said mixture of phenols from said solvent by distilling to provide said purified natural cresylic acid mixture as an overhead product and said solvent as a bottoms product; and d. recycling said solvent to step b.

2. A process as recited in claim 1 wherein said step of recycling said solvent further includes the step of distilling at least a portion of said solvent bottoms product from step c to remove impurities therefrom prior to said recycle step d.

3. A process as recited in claim 1 wherein said feedstock contains water and wherein said feedstock is distilled to remove said water content prior to step b.

4. A process as recited in claim 1 wherein said feedstock is processed to remove at least a portion of said tar base substances prior to step b.

5. A process as recited in claim 1 wherein said polyhydric alcohol solvent is triethylene glycol.

* * * * *